United States Patent [19]

Sharifian et al.

[11] Patent Number: 4,904,357
[45] Date of Patent: Feb. 27, 1990

[54] PRODUCTION OF QUATERNARY AMMONIUM AND QUATERNARY PHOSPHONIUM BOROHYDRIDES

[75] Inventors: Hossein Sharifian; John S. Dutcher, both of Austin, Tex.

[73] Assignee: Southwestern Analytical, Houston, Tex.

[21] Appl. No.: 358,884

[22] Filed: May 30, 1989

[51] Int. Cl.$^4$ .............................. C25B 3/00; C25B 3/04
[52] U.S. Cl. .................................... 204/73 R; 204/72; 204/101; 204/182.3; 204/182.4
[58] Field of Search ............ 204/72, 73 R, 101, 182.3, 204/182.4

[56] References Cited

U.S. PATENT DOCUMENTS 3,734,842  5/1971  Cooper .................................. 204/86
4,572,769  2/1986  Shimizu ................................ 204/72

Primary Examiner—John F. Niebling
Assistant Examiner—Steven P. Marquis
Attorney, Agent, or Firm—Renner, Otto, Boisselle & Sklar

[57] ABSTRACT

A process is described for preparing quaternary ammonium and quaternary phosphonium borohydrides in an electrolysis cell which comprises an anolyte compartment containing an anode and a catholyte compartment containing a cathode, the anolyte and catholyte compartments being separated from each other by a divider, said process comprising (A) charging an anolyte comprising an aqueous solution containing a quaternary ammonium or a quaternary phosphonium salt compound to the anolyte compartment;

(B) charging a catholyte comprising an aqueous solution prepared from a quaternary ammonium borohydride or the quaternary phosphonium boron oxide to the catholyte compartment;

(C) passing a current through the electrolysis cell to produce the quaternary ammonium borohydride or the quaternary phosphonium borohydride in the catholyte compartment; and (D) removing at least a portion of the catholyte from the catholyte compartment.

The quaternary ammonium and quaternary phosphonium borohydrides can be recovered from the catholyte removed in ste (D) from the catholyte.

In one preferred embodiment, quaternary ammonium borohydrides are prepared utilizing quaternary ammonum boron oxides in the aqueous catholyte and quaternary ammonium compounds such as quaternary ammonium hydroxides in the anolyte solution.

52 Claims, 1 Drawing Sheet

PRODUCTION OF QUATERNARY AMMONIUM AND QUATERNARY PHOSPHONIUM BOROHYDRIDES

TECHNICAL FIELD

This invention relates to an electrolytic process for preparing quaternary ammonium and quaternary phosphonium borohydrides from the corresponding boron oxides.

BACKGROUND OF THE INVENTION

U.S. Pat. No. 3,734,842 describes an electrolytic process for the production of alkali metal borohydrides wherein borate ions are reduced to borohydride ions. In particular, the process utilizes an electrolytic cell having a cationic-selective membrane separating the anode and cathode compartments, and the reduction of borate ions to borohydride ions occurs in the cathode compartment to produce alkali metal borohydride solution from which the borohydride material may be separated. The borate ions utilized in the catholyte solutions of the process are derived from alkali metal metaborate, alkali metal tetraborate, borax, and boric acid. The anolyte solution utilized in the anolyte compartment comprises an aqueous solution of an alkali metal hydroxide, alkali metal chloride, alkali metal sulfate or alkali metal carbonate.

SUMMARY OF THE INVENTION

A process is described for preparing quaternary ammonium and quaternary phosphonium borohydrides in an electrolysis cell which comprises an anolyte compartment containing an anode and a catholyte compartment containing a cathode, the anolyte and catholyte compartments being separated from each other by a divider, said process comprising (A) charging an anolyte comprising an aqueous solution containing a quaternary ammonium or quaternary phosphonium salt compound to the anolyte compartment;

(B) charging a catholyte comprising an aqueous solution prepared from a quaternary ammonium or a quaternary phosphonium boron oxide to the catholyte compartment;

(C) passing a current through the electrolysis cell to produce the quaternary ammonium borohydride or quaternary phosphonium borohydride in the catholyte compartment; and (D) removing at least a portion of the catholyte from the catholyte compartment. The quaternary ammonium borohydride and quaternary phosphonium borohydride can be recovered from the catholyte.

In one preferred embodiment, quaternary ammonium borohydrides are prepared utilizing quaternary ammonium boron oxides in the aqueous catholyte and quaternary ammonium compounds such as quaternary ammonium hydroxide in the anolyte solution.

DESCRIPTION OF THE PREFERRED EMBODIMENTS

Figure 1:
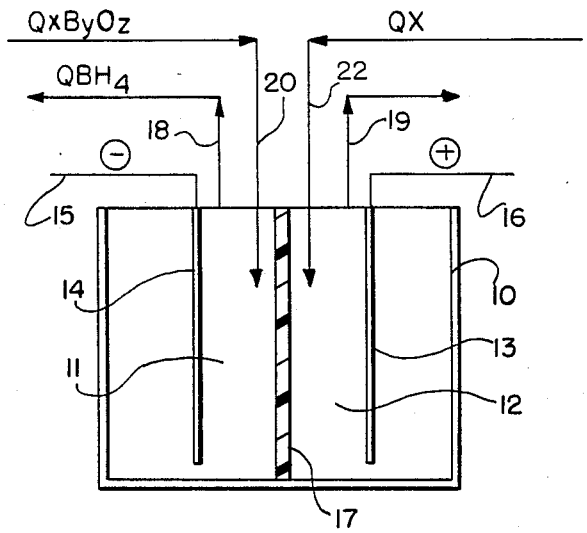
FIG. 1 is a schematic cross-section of an electrolytic cell useful in performing the process for preparing the borohydrides of the invention.

The borohydride compounds which can be prepared in accordance with the process of the present invention may be characterized by the following formulae

  (IIIA)

  (IIIB)

wherein $R_1$, $R_2$, $R_3$ and $R_4$ are each independently alkly group containing from 1 to about 10 carbon atoms, hydroxyalkyl groups or alkoxyalkyl groups containing from about 2 to about 10 carbon atoms, aryl groups, or $R_1$ and $R_2$, together with the N or P atom may form a heterocyclic group provided that if the heterocyclic group contains a —C=N— or —C=P— bond, $R_3$ is the second bond.

In one preferred embodiment, $R_1$, $R_2$, $R_3$ and $R_4$ are each independently alkyl groups containing from 1 to about 10 carbon atoms and more generally from about 1 to about 4 carbon atoms. Specific examples of alkyl groups include methyl, ethyl, n-propyl, n-butyl, n-pentyl, n-hexyl, n-heptyl, n-octyl, n-nonyl and n-decyl groups. Preferred examples of alkyl groups include methyl, ethyl and butyl groups. $R_1$, $R_2$, $R_3$ and $R_4$ also may be hydroxyalkyl groups such as hydroxyethyl and the various isomers of hydroxypropyl, hydroxybutyl, hydroxypentyl, etc. Specific examples of alkoxyalkyl groups include methoxymethyl, ethoxymethyl, ethoxyethyl, butoxyethyl, butoxybutyl, etc. The aryl groups may be substituted aryl groups as well as unsubstituted aryl groups, and the substituted may be any substituent which does not interfere with the process of the present invention. Examples of various aryl useful as $R_1$, $R_2$, $R_3$ and $R_4$ include phenyl, benzyl, and equivalent groups wherein benzene rings have been substituted with one or more hydroxy groups.

Any two of groups $R_1$ through $R_4$ may comprise alkylene groups joined together with the N or P atom to form a heterocyclic group containing 2 or more carbon atoms, preferably 2 to 6 carbon atoms, and more preferably 4 to 5 carbon atoms, provided that if the heterocyclic group contains a —C=N— or a —C=P— bond, a third R group is the second bond. Examples of such heterocyclic groups include aziridines and phosphiranes (2 carbon atoms), azetidines and phosphetanes (3 carbon atoms) pyrrolidines and phospholanes (4 carbon atoms), piperidines and phosphanes (5 carbon atoms).

Specific examples of quaternary ammonium borohydrides represented by Formulae IIIA, which can be prepared in accordance with the process of the present invention include tetramethylammonium borohydride, tetraethylammonium borohydride, tetrapropylammonium borohydride, tetrabutylammonium borohydride, trimethylhydroxyethylammonium borohydride, dimethyldihydroxyethylammonium borohydride, methyltrihydroxyethylammonium borohydride, phenyltrimethylammonium borohydride, phenyltriethylammonium borohydride, benzyltrimethylammonium borohydride, N,N-dimethyl-pyrrolidinium borohydride, N,N-diethyl-pyrrolidinium borohydride, N,N-dimethyl-piperidinium borohydride, N,N-diethyl-piperidinium borohydride, etc.

Examples of quaternary phosphonium borohydrides is represented by Formula IIIB which may be prepared in accordance with the process of the present invention include tetramethylphosphonium borohydride, tetraethylphosphonium borohydride, tetrapropylphosphonium borohydride, tetrabutylphosphonium borohydride, trimethylhydroxyethylphosphonium borohydride, dimethyldihydroxyethylphosphonium borohydride, methyltrihydroxyethylphosphonium borohydride, phenyltrimethylphosphonium borohydride, phenyltriethylphosphonium borohydride, benzyltrimethylphosphonium borohydride.

The above-described borohydrides represented by Formulae IIIA and IIIB are prepared by the electrolysis and reduction of the corresponding ammonium or phosphonium boron oxide compounds which may generically be represented by the formula $$Q_xB_yO_z \qquad (II)$$

wherein Q represents a quaternary ammonium ion or a quaternary phosphonium ion; B is boron; O is oxygen; x is 1 or 2; y is 1 or 4; and z is 2, 3 or 7. When x and y are 1 and z is 2 ($QBO_2$), the compound is a metaborate; when x is 2, y is 4 and z is 7 ($Q_2B_4O_7$), the compound is a tetraborate; and when x is 1, y is 1 and z is 3 ($QBO_3$), the compound is a perborate.

Accordingly, the quaternary ammonium boron oxide compounds useful as starting materials present in the catholyte may be of the following generic types.

$$[(R_1R_2R_3R_4)N]^+BO_2^{31} \qquad (IIA)$$

$$[(R_1R_2R_3R_4)N]^+BO_3^{31} \qquad (IIA)$$

$$[(R_1R_2R_3R_4)N]^+{}_2B_4O_7^= \qquad (IIC)$$

wherein $R_1$, $R_2$, $R_3$ and $R_4$ are as defined with respect to Formula IIIA. The catholyte solutions may be prepared from the above-described types of boron oxides or available hydrates thereof. Formulae similar to the above can also be written to represent the phosphonium boron oxides utilized as reactants in the process of the present invention. In one preferred embodiment, the boron oxide compounds can be prepared by reacting a quaternary ammonium or phosphonium salt with boric acid or boric acid anhydride.

Specific examples of quaternary ammonium boron oxides as represented generically by Formula II, more particularly by Formulae IIA-C, include tetramethylammonium metaborate, tetramethylammonium tetraborate, tetramethylammonium perborate, tetraethylammonium metaborate, tetraethylammonium tetraborate, tetramethylammonium perborate, tetrabutylammonium metaborate, tetrabutylammonium tetraborate, tetrabutylammonium perborate, trimethylhydroxyethylammonium metaborate, dimethyldihydroxyethylammonium metaborate, phenyltrimethylammonium metaborate, phenyltriethylammonium metaborate, benzyltrimethylammonium metaborate, N,N-dimethyl-pyrrolidinium metaborate, etc.

Examples of quaternary phosphonium boron oxides which can be utilized as reactants in the process of the present invention include tetramethylphosphonium metaborate, tetramethylphosphonium metaborate, tetrapropylphosphonium metaborate, tetrabutylphosphonium metaborate, tetrabutylphosphonium perborate, trimethylhydroxyethylphosphonium metaborate, dimethyldihydroxyethylphosphonium metaborate, phenyltriethylphosphonium metaborate, etc.

The above-described boron oxides are utilized in the process of the present invention as a component in the catholyte solution which is charged to the catholyte compartment. The concentration of the boron oxide compound in the catholyte may vary over a wide range and may even be present in major amount. Generally, however, from about 1 to about 40% by weight of the boron oxide compound is present in the aqueous catholyte solution. It is desirable that the catholyte solution is alkaline to stabilize the borohydride as it is formed. The migration of the cations from the anolyte to the catholyte increases the alkalinity of the catholyte.

The compound contained in the aqueous anolyte charged to the anolyte compartment in the process of the present invention is generically described as a quaternary ammonium or quaternary phosphonium salt compound. The salt compound may be a hydroxide, halide, carbonate, alkyl carbonate, formate, sulfate, hydrogen sulfate, phosphate, hydrogen phosphate, dihydrogen phosphate, etc.

The concentration of such compound in the anolyte solution charged to the anolyte compartment may also vary over a wide range and may even be present in a major amount. Generally, however, the concentration of the salt compound in the anolyte solution ranges from about 3 to about 40% by weight.

In one embodiment, the quaternary ammonium and quaternary phosphonium salt compounds contained in the anolyte are represented by the following formulae:

$$[(R_1R_2R_3R_4)N^+]_aX^{-a} \qquad (IA)$$

$$[(R_1R_2R_3R_4)P^+]_aX^{-a} \qquad (IB)$$

wherein $R_1$, $R_2$, $R_3$ and $R_4$ are each independently alkyl or alkoxyalkyl groups containing from 1 to about 10 carbon atoms, hydroxyalkyl groups containing from about 2 to about 10 carbon atoms, aryl groups (including hydroxy aryl groups) or $R_1$ and $R_2$, together with the N or P atom may form a saturated heterocyclic group containing 4 or 5 carbon atoms;

X is a hydroxide, halide, carbonate, alkyl carbonate, formate, phosphate or sulfate ion; and a is a number equal to the valence of X.

In one embodiment, the hydroxides and carbonates are preferred. The quaternary ammonium and quaternary phosphonium groups present in the compounds charged to the anolyte may correspond to any of the quaternary ammonium or quaternary phosphonium groups described above with respect to the boron oxides and borohydrides. Exemplary compounds include tetramethylammonium hydroxide, tetraethylammonium hydroxide, tetrabutylammonium hydroxide, tetramethylammonium, chloride, tetramethylammonium bromide, tetramethylammonium iodide, tetramethylammonium carbonate, tetrabutylammonium carbonate, tetramethylammonium carbonate, tetramethylammonium sulfate, tetrabutylammonium sulfate, tetrabutylammonium carbonate, tetramethylammonium phosphate, tetramethylammonium hydrogen phosphate, tetramethylammonium dihydrogen phosphate, tetramethylammonium sulfate, tetramethylammonium hydrogen sulfate, tetramethylphosphonium chloride, tetramethylphosphonium bromide, tetramethylphosphonium iodide, tetramethylphosphonium hydroxide, tetramethylphosphonium carbonate.

In the process of the present invention, (A) an anolyte comprising an aqueous solution containing a quaternary ammonium or quaternary phosphonium salt compound as defined above is charged to the anolyte compartment;

(B) a catholyte comprising an aqueous solution containing a quaternary ammonium or quaternary phosphonium boron oxide is charged to the catholyte compartment;

(C) a current is passed through the electrolysis cell to produce the quaternary ammonium or the quaternary phosphonium borohydride in the catholyte compartment; and (D) at least a portion of the catholyte is removed from the catholyte compartment.

The phrase "aqueous solution" above is defined herein to include aqueous solutions in which the aqueous component may include deuterium oxide ($D_2O$, also known as "heavy water"), tritium oxide ($T_2O$), or a mixture of $D_2O$ and $T_2O$. The afore-mentioned process conducted using $D_2O$ and/or $T_2O$ produces borohydrides which contain a roughly equivalent amount of deuterium and/or tritium anions as the hydride component of the borohydride produced in step (C). The aqueous component of the aqueous solution may be pure, or substantially pure, $D_2O$ and/or $T_2O$, or may be present in ordinary water in an amount greater than their natural abundance. Depending on the intended percentage of deuterium and/or tritium anions in the borohydride, $D_2O$ may, for example, be present in an amount from as low as about 0.02 mole percent to 99.9 mole percent $D_2O$ relative to the amount of ordinary $H_2O$ present in order to be considered enriched with $D_2O$. The amount of $T_2O$ present may be adjusted relative to deuterium and/or hydrogen so that the borohydride product produced therefrom produces a detectable amount of radiation from the decay of the tritium anion. The aqueous component may, for example, contain an amount of $T_2O$ above natural abundance up to about 10 mole percent or more.

The borohydride-containing catholyte obtained in step (D) from the catholyte compartment may be used without separation of the borohydride in some applications. For example, the solution can be used in the reductive bleaching of paper pulp and for reducing various organic compounds. The solution also can be used in the operation of a fuel cell using the borohydride as the fuel source. Where the borohydride is needed in a more concentrated form, the withdrawn catholyte solution can be concentrated, or the borohydride can be isolated from the solution such as by crystallization, evaporation, etc.

In addition to the utilities set forth above, when the hydride component of the borohydride-containing catholyte obtained in step (D) is obtained from a $D_2O$ and/or $T_2O$ enriched aqueous solution, the borohydride-containing catholyte is useful as an agent for transferring deuterium or tritium to another agent or compound which is capable of accepting the deuterium or tritium from the borohydride during reduction. The deuterium and/or tritium labeled borohydride may, for example, be used to transfer deuterium or tritium to an organic compound, such as a pharmaceutical, for detection or tracing purposes. Tritium, for example, is commonly used as a label for tracing the metabolic passways of organic compounds in biological systems due to the ability to detect the small amount of low level radioactivity generated by the decay of tritium into lighter forms of hydrogen. Deuterium is often used, for example, in the detection or tracing of organic compounds in humans, since it is undesirable to expose humans to radio-labeled compounds. Deuterium-labeled compounds may be detected using mass spectrometry.

The presence of deuterium in certain pharmaceuticals is also capable of slowing down metabolization of that pharmaceutical to achieve a longer lasting effect, and the presence of deuterium sometimes decreases a pharmaceutical's toxicity by changing the pharmaceutical's metabolic pathway.

Various materials which have been used as anodes in electrolysis cells can be included in the cells used in the above and other embodiments of the present invention provided they do not react with the solution added to the cells. For example, the anode may be made of high purity graphite or metals such as, for example, titanium-coated or clad electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

Various materials which have been used as cathodes in electrolytic cells can be included in the cells used in the above and other embodiments of the present invention. Cathode materials include nickel, iron, stainless steel, nickel plated titanium, platinum, etc., and alloys thereof. The term "alloy" is used in a broad sense and includes intimate mixtures of two or more metals as well as one metal coated onto another metal. The above-described anode and cathode materials may be coated or dispersed on a metal or inert substrate to form the desired anode or cathode.

During the electrolysis, it is desirable that the temperature within the liquid of the cell be maintained in the range of from about 10° C. to about 70° C., and more generally, the temperature is maintained at about 50° C. or below during electrolysis.

Electrolysis is effected by impressing a current voltage (generally a direct current) between the anode and the cathode with a current density of from about 5 to about 250 $A/ft^2$, and more preferably at a current density of from about 25 to about 150 $A/ft2$. Alternatively, the current density may be from about 1–100 $A/dm^2$ or 10–50 $A/dm^2$. The current density is applied to the cell for a period of time which is sufficient to result in the desired reaction and production of the borohydride. In practice, the electrolytic cell can be operated batchwise or in a continuous operation.

The process of the present invention is conducted in an electrolytic cell which comprises an anolyte compartment containing an anode and a catholyte compartment containing a cathode, the anolyte and catholyte compartments being separated from each other by a diffusion barrier or divider.

The divider in the electrolytic cells used in this invention may be any material which functions as a gas separator. Examples of such divider materials include inert fabrics, sintered glass, ceramics, and membrane diaphragms. Membrane diaphragms are particularly useful and are preferred. The membrane dividers are preferably cation-exchange membranes.

The cationic membranes utilized in electrolytic cells and in the process of the present invention comprise a highly durable material such as the membrane based on the fluorocarbon series, or from less expensive materials of the polystyrene or polypropylene series. Preferably, however, the cationic membranes useful in the present invention include fluorinated membranes containing cation-exchange groups such as perfluorosulfonic acids and perfluorosulfonic acid/perfluorocarboxylic acid, perfluorocarbon polymer membranes such as those sold by the E.I. DuPont Nemours and Company under the trade designation "Nafion". Other suitable cation-exchange membranes include styrene-divinyl benzene copolymer membranes containing cation-exchange groups such as sulfonate groups, carboxylate groups, etc.

The type of electrolysis cell used in the process of the present invention is not critical and may be any of the known electrolysis cells. The cells may be composed of conventional cell materials which are compatible with the materials being charged into the compartments.

The application of the current through the cell results in the reduction of the boron oxide compound contained in the catholyte to the corresponding borohydride. At the anode, the quaternary ammonium or quaternary phosphonium compound is ionized, and the cations (i.e., quaternary ammonium cations or quaternary phosphonium cations) migrate through the membrane into the catholyte solution. When the anion in the anolyte is a hydroxide ion, oxygen is evolved and escapes from the anolyte compartment. Similarly, when the anion in the anolyte is a halide, halogen is evolved, and when the anion is a carbonate, carbon dioxide is evolved.

The reactions which occur during electrolysis are illustrated as follows utilizing tetramethylammonium borate and tetramethylammonium hydroxide as the reactants.

At the cathode:

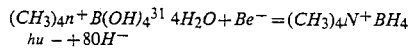

At the anode:

$$4H_2O = 8H^+ + 2O_2 + 8e^-  \quad (2)$$

Overall reaction:

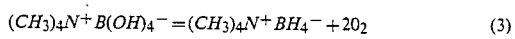

A schematic cross-section or representation of an electrolytic cell useful in the process of the present invention is shown in FIG. 1. In FIG. 1, the electrolytic cell 10 comprises a catholyte compartment 11 and an anolyte compartment 12 separated from each other by a divider 17 such as a cationic selective membrane. The catholyte compartment 11 contains cathode 14 which is attached to a power supply (not illustrated) by wire 15. The anolyte compartment 12 contains anode 13 which is attached to a power supply (not illustrated) through wire 16. With reference to FIG. 1, the anolyte QX is supplied to the anolyte compartment as illustrated by line 22, and the catholyte comprising an aqueous solution of $Q_xB_yO_z$ is supplied to the catholyte compartment as shown by line 20. After passage of a direct current through the electrolysis cell whereby the desired borohydride is formed in the catholyte, at least a portion of the catholyte containing the borohydride ($QBH_4$) and some unreacted boron oxide is withdrawn as shown by line 18 and the borohydride can be recovered from the catholyte. The anolyte which is depleted in QX compound is removed as shown by line 19.

Figure 2:
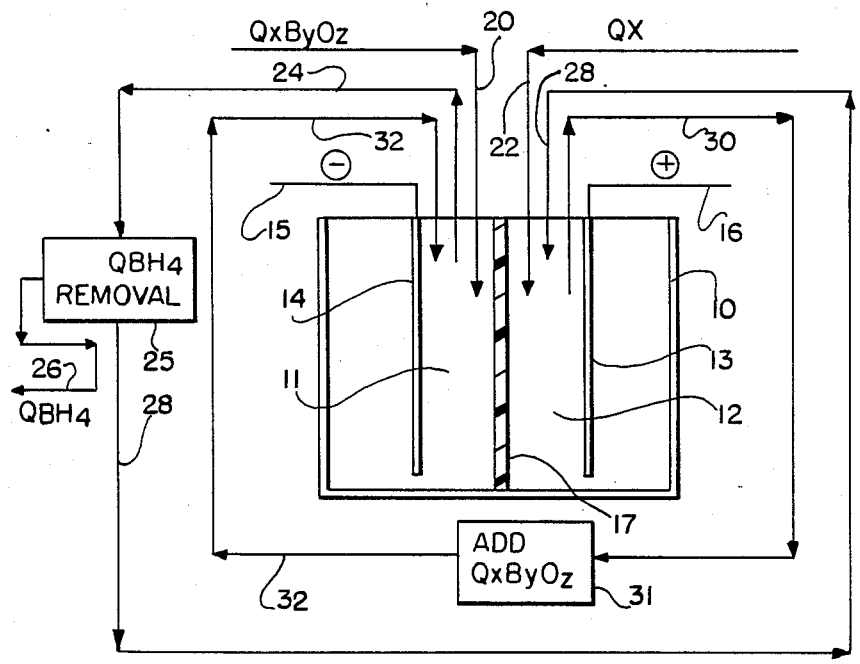
FIG. 2 is a schematic cross-section of one preferred process and electrolytic cell comprising a closed loop.

One preferred example of the process utilized in the present invention for preparing the desired borohydrides is illustrated in the flow diagram of FIG. 2 which provides a closed loop with resulting favorable economics of operation. In FIG. 2, the electrolytic cell 10 comprises a catholyte compartment 11 and an anolyte compartment 12 separated from each other by cationic selective membrane 17. The catholyte compartment 11 contains a cathode 14 which is attached to a power supply (not illustrated) by wire 15. The anolyte compartment 12 contains cathode 13 which is attached to a power supply (not illustrated) through wire 16. A catholyte comprising an aqueous solution of a boron oxide represented by Formula $Q_xB_yO_z$ is charged to the catholyte compartment as shown by line 20, and an anolyte comprising an aqueous solution of the compound represented by QX is charged to the anolyte compartment as shown by line 22. When a current is passed through the electrolysis cell, the boron oxide compound in the catholyte is reduced to the desired borohydride and the cation $Q^+$ passes from the anolyte compartment to the catholyte compartment through membrane 17 resulting in a catholyte enriched in $Q^+$.

In the closed system illustrated in FIG. 2, after the current is passed through the electrolysis cell and quaternary borohydride is formed in the catholyte, at least a portion of the catholyte is withdrawn from the catholyte compartment as shown by line 58 to a borohydride recovery zone 25. The catholyte which is withdrawn from the catholyte compartment and transferred to recovery zone 25 contains the desired borohydride $QBH_4$, unreacted boron oxide and QOH. Because the borohydride is less soluble in water than the boron oxide or the QOH compound, the desired borohydride product may be separated from the solution by known techniques such as crystallization, filtration or extraction. Thus, the desired borohydride is removed from the loop as shown by line 26, and the solution which remains after removal of the desired borohydride is recycled and charged to the anolyte compartment as shown by line 28.

The anolyte contained in anolyte compartment 12, after electrolysis, contains a reduced amount of $Q^+$ as a result of the passage of these cations through the cation exchange membrane 17 into the catholyte compartment as described above, and at least a portion of this anolyte is removed from the anode compartment as shown by line 30 and transferred to a boron oxide compound makeup zone 31 where the concentration of the boron oxide compound is increased to the desired operating level for recycle and is charged to the catholyte compartment as shown by line 32.

The process of the present invention and the results obtained from the process can be enhanced by adding a hydrogenation catalyst to the cathode compartment. The hydrogenation catalyst generally is added to the cathode compartment as a powder, flake, pellets or granules which are maintained within the cathode compartment by means of the divider. The hydrogenation catalyst may be distributed throughout the cathode compartment or the hydrogenation catalyst may be maintained in contact with the cathode (sometimes referred to as a fixed bed cathode). The hydrogenation catalyst used in the process of the present invention may be any of the many hydrogenation catalysts known in the art. Preferred examples include nickel, cobalt, copper, platinum, palladium, rhodium, or alloys, compounds or mixtures thereof. The hydrogenation catalyst incorporated into the cathode compartment may be the same as or different from the cathode material.

The following examples illustrate the process of the present invention utilizing a quaternary ammonium borate (tetramethylammonium borate) and a quaternary ammonium hydroxide (tetramethylammonium hydroxide) as reactants. Similar processes can be conducted utilizing other quaternary ammonium borates in the catholyte and quaternary ammonium salt compounds as described above in the anolyte. The processes described in the following examples also can be carried out utilizing any of the quaternary phosphonium boron oxides and salt compounds described above. It should be apparent that if a quaternary ammonium boron oxide is utilized in the catholyte, the compound incorporated into the anolyte solution should be a quaternary ammonium compound. Similarly, when the boron oxide incorporated into the catholyte is a quaternary phosphonium boron oxide, the compound utilized in the anolyte should be a quaternary phosphonium compound. It is generally preferred that the groups $R_1$, $R_2$, $R_3$ and $R_4$ in the anolyte and catholyte solutions for any given process be identical.

Unless otherwise indicated in the following examples, and elsewhere in the specification and claims, all parts and percentages are by weight, all temperatures are in degrees Celsius, and pressure is at or near atmospheric pressure.

EXAMPLE 1

An electrolytic cell is prepared in accordance with the present invention wherein the anode is a platinum clad anode with a surface area of 40 $cm^2$, and the cathode is platinum clad with a surface area of 40 $cm^2$. Nickel boride particles (35 mesh) are added to the catholyte compartment, and the particles are maintained in contact with the cathode. An aqueous anolyte (100 ml.) of 25% tetramethylammonium hydroxide is charged to the anode compartment, and an aqueous catholyte solution (100 ml.) of tetramethylammonium borate (7%) is charged to the cathode compartment. The anolyte and catholyte compartments are separated by means of a cationic membrane (Nafion 901). The electrolysis is carried out at 50 $mA/cm^2$ for a period of two hours. A current efficiency of 80% is achieved for the synthesis of tetramethyl ammonium borohydride. Because of the considerably lower solubility of tetramethylammonium borohydride in water than tetramethylammonium hydroxide or tetramethylammonium borate, the tetramethylammonium hydroxide is separated by a crystallization step through a lowering of the temperature of the catholyte solution which has been removed from the catholyte compartment. Crystallization also can be enhanced by the addition of a further quantity of tetramethylammonium hydroxide to the recovered catholyte solution.

EXAMPLE 2

The procedure of Example 1 is repeated except that the catholyte compartment is filled with nickel powder. The electrolysis is carried out the current density of 50 $mA/cm^2$ for a period of two hours. A current efficiency of 45% is achieved for the synthesis of the tetramethylammonium borohydride which is recovered by crystallization.

EXAMPLE 3

The procedure of Example 1 is repeated except that no catalyst particles are introduced into the catholyte compartment. The electrolysis is carried out at a current density of 50 $mA/cm^2$ for a period of two hours. The current efficiency of 8% is obtained for the electrosynthesis of tetramethylammonium borohydride which is recovered by crystallization of the catholyte solution.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for preparing quaternary ammonium and quaternary phosphonium borohydrides in an electrolysis cell which comprises an anolyte compartment containing an anode and a catholyte compartment containing a cathode, the anolyte and catholyte compartments being separated from each other by a divider, said process comprising
   (A) charging an anolyte comprising an aqueous solution containing a quaternary ammonium or a quaternary phosphonium salt compound to the anolyte compartment;
   (B) charging a catholyte comprising an aqueous solution prepared from a quaternary ammonium boron oxide or a quaternary phosphonium boron oxide to the catholyte compartment;
   (C) passing a current through the electrolysis cell to produce the quaternary ammonium borohydride or quaternary phosphonium borohydride in the catholyte compartment; and
   (D) removing at least a portion of the catholyte from the catholyte compartment.

2. The process of claim 1 wherein the quaternary ammonium or quaternary phosphonium salt compound used to prepare the anolyte solution charged in step (A) is a hydroxide, halide, carbonate, alkyl carbonate, formate, phosphate, or sulfate.

3. The process of claim 1 wherein the boron oxide used to prepare the aqueous catholyte solution charged in step (B) is a metaborate, tetraborate, perborate, borate or the hydrates, anhydrides or mixtures thereof.

4. The process of claim 1 wherein at least one hydrogenation catalyst is present in the catholyte compartment.

5. The process of claim 4 wherein the hydrogenation catalyst is nickel, cobalt, rhodium, copper, platinum, palladium or alloys, compounds or mixtures thereof.

6. The process of claim 1 wherein the divider is a cation exchange membrane.

7. The process of claim 6 wherein the cation exchange membrane comprises a perfluorosulfonic acid or a perfluorosulfonic acid/perfluorocarboxylic acid perfluorocarbon polymer membrane.

8. The process of claim 1 wherein (E) the quaternary ammonium or phosphonium borohydride is recovered from the catholyte solution.

9. The process of claim 8 wherein the solution obtained in step (E) after the borohydride is recovered from the catholyte solution is charged to the anolyte compartment as anolyte.

10. The process of claim 1 wherein at least a portion of the anolyte is removed from the anolyte compartment after step (C); quaternary ammonium or quaternary phosphonium boron oxide is added to the removed anolyte solution; and the boron oxide enriched solution is charged to the catholyte compartment as catholyte.

11. The process of claim 1 wherein the quaternary ammonium and the quaternary phosphonium compounds contained in the anolyte are characterized by the formula $$[(R_1R_2R_3R_4)N^+]_a X^{-a} \quad \text{(IA)}$$

or $$[(R_1R_2R_3R_4)P^+]_a X^{-a} \quad \text{(IB)}$$

wherein $R_1$, $R_2$, $R_3$ and $R_4$ are each independently alkyl groups containing from 1 to about 10 carbon atoms, hydroxyalkyl or alkoxyalkyl groups containing from about 2 to about 10 carbon atoms, aryl groups, or $R_1$ and $R_2$, together with the N or P atom may form a heterocyclic group provided that if the heterocyclic group contains a —C=N— bond, $R_3$ is the second bond;

X is a hydroxide, halide, formate, carbonate, alkyl carbonate, phosphate or sulfate ion; and a is a number equal to the valence of X.

12. The process of claim 11 wherein $R_1$, $R_2$, $R_3$ and $R_4$ are each independently alkyl groups containing from 1 to 4 carbon atoms.

13. The process of claim 11 wherein $R_1$, $R_2$, $R_3$ and $R_4$ are methyl groups.

14. The process of claim 1 wherein a direct current is passed through the electrolysis cell in step (C).

15. The process of claim 1 wherein the anolyte charged in step (A) contains from about 3 to about 40% by weight of the quaternary compound.

16. The process of claim 1 wherein the catholyte charged in step (B) is prepared with from about 1 to about 40% by weight of the boron compound.

17. The process of claim 1 wherein the anolyte charged in step (A) and the catholyte charged in step (B) together comprise at least about 0.02 mole percent deuterium oxide.

18. The process of claim 1 wherein the anolyte charged in step (A) and the catholyte charged in step (B) together comprise at least about 10 mole percent deuterium oxide.

19. The process of claim 1 wherein the anolyte charged in step (A) and the catholyte charged in step (B) together comprise an amount of tritium oxide which is greater than that which is naturally occurring.

20. The process of claim 1 wherein the anolyte charged in step (A) and the catholyte charged in step (B) together comprise at least about 0.1 mole percent tritium oxide.

21. A process for preparing quaternary ammonium borohydrides in an electrolysis cell which comprises an anolyte compartment containing an anode and a catholyte compartment containing a cathode, the anolyte and catholyte compartments being separated from each other by a cation exchange membrane, said process comprising (A) charging an anolyte comprising an aqueous solution containing a quaternary ammonium compound selected from the group of quaternary ammonium hydroxide, halide, formate, sulfate, phosphate, carbonate or alkyl carbonate to the anolyte compartment;

(B) charging a catholyte comprising an aqueous solution prepared from a quaternary ammonium boron oxide to the catholyte compartment;

(C) passing a current through the electrolysis cell to produce the quaternary ammonium borohydride in the catholyte compartment; and (D) removing at least a portion of the catholyte from the catholyte compartment.

22. The process of claim 21 wherein the quaternary ammonium boron oxide used to make the catholyte solution charged in step (B) is a borate, metaborate, tetraborate or perborate, or the hydrates, anhydrides, or mixtures thereof.

23. The process of claim 21 wherein at least one hydrogenation catalyst is present in the catholyte compartment.

24. The process of claim 23 wherein the hydrogenation catalyst is nickel, cobalt, rhodium, copper, platinum, palladium or alloys, compounds or mixtures thereof.

25. The process of claim 21 wherein (E) the quaternary ammonium borohydride is recovered from the catholyte solution removed in step (D).

26. The process of claim 21 wherein the catholyte solution which remains after the quaternary ammonium borohydride is recovered in step (E) is charged to the anolyte compartment as anolyte.

27. The process of claim 21 wherein at least a portion of the anolyte is removed from the anolyte compartment after step (C); quaternary ammonium boron oxide is added to the removed anolyte solution; and the solution is charged to the catholyte compartment as catholyte.

28. The process of claim 21 wherein the quaternary ammonium compound in the anolyte charged in step (A) is characterized by the formula $$[(R_1R_2R_3R_4)N^+]_a X^{-a} \quad \text{(IA)}$$

wherein $R_1$, $R_2$, $R_3$ and $R_4$ are each independently alkyl groups containing from 1 to about 10 carbon atoms, hydroxyalkyl or alkoxyalkyl groups containing from about 2 to about 10 carbon atoms, aryl groups, or $R_1$ and $R_2$, together with the N may form a heterocyclic group, provided that, if the heterocyclic group contains a —C=N— group, $R_3$ is the second bond;

X is a hydroxide, halide, formate, carbonate, alkyl carbonate, phosphate or sulfate ion; and a is a number equal to the valence of X.

29. The process of claim 28 wherein X is a hydroxide or chloride ion.

30. The process of claim 28 wherein X is hydroxide.

31. The process of claim 28 wherein $R_1$, $R_2$, $R_3$ and $R_4$ are each independently alkyl groups containing from 1 to 4 carbon atoms.

32. The process of claim 28 wherein $R_1$, $R_2$, $R_3$ and $R_4$ are methyl groups.

33. The process of claim 21 wherein a direct current is passed through the electrolysis step in step (C).

34. The process of claim 21 wherein the anolyte charged in step (A) contains from about 3 to about 40% by weight of the quaternary ammonium compound.

35. The process of claim 21 wherein the catholyte charged in step (B) is prepared with from about 1 to about 40% by weight of the quaternary ammonium boron oxide compound.

36. The process of claim 21 wherein the cation exchange membrane comprises a perfluorosulfonic acid or a perfluorosulfonic acid/perfluorocarboxylic acid perfluorocarbon polymer membrane.

37. The process of claim 36 wherein the catholyte charged in step (B) comprises an aqueous solution prepared with a quaternary ammonium borate and a quaternary ammonium hydroxide.

38. The process of claim 21 wherein the anolyte charged in step (A) comprises an aqueous solution of quaternary ammonium chloride which upon electrolysis liberates chlorine at the anode.

39. The process of claim 21 wherein the catholyte is an aqueous solution comprising quaternary ammonium metaborate and a quaternary ammonium hydroxide.

40. A process for preparing a quaternary ammonium borohydride in an electrolysis cell which comprises an anolyte compartment containing an anode and a catholyte compartment containing a cathode, the anolyte and catholyte compartments being separated from each other by a cation exchange membrane, said process comprising (A) charging an anolyte comprising an aqueous solution containing from about 3 to about 40% by weight of a quaternary ammonium hydroxide to the anolyte compartment, said quaternary ammonium hydroxide being characterized by the formula $$[(R_1R_2R_3R_4)N]^+OH^- \quad \text{(IC)}$$

(B) charging an aqueous solution prepared with from about 1 to about 40% by weight of a quaternary ammonium boron oxide to the catholyte compartment, said quaternary ammonium boron oxide being characterized by the formula $$[(R_1R_2R_3R_4)N]_xB_yO_z \cdot mH_2O \quad \text{(IIA)}$$

(C) passing a direct current through the electrolysis cell to produce the quaternary ammonium borohydride represented by the formula $$[(R_1R_2R_3R_4)N]^+BH_4^- \quad \text{(IIIA)}$$

in the catholyte wherein $R_1$, $R_2$, $R_3$ and $R_4$ in Formulae IC, IIA and IIIA are each independently alkyl groups containing from 1 to about 10 carbon atoms, or hydroxyalkyl groups containing from 2 to about 10 carbon atoms; x is 1 or 2; y is 1 or 4; z is 2, 3 or 7; and m is 0 or an integer equal to the number of moles of water of hydration; and (D) removing at least a portion of the catholyte containing quaternary ammonium borohydride from the catholyte compartment.

41. The process of claim 40 wherein $R_1$, $R_2$, $R_3$ and $R_4$ are each independently alkyl groups containing from 1 to 4 carbon atoms.

42. The process of claim 40 wherein $R_1$, $R_2$, $R_3$ and $R_4$ are methyl groups.

43. The process of claim 40 wherein x is 1, y is 1, and z is 2.

44. The process of claim 40 wherein the quaternary ammonium boron oxide used to prepare the solution charged to the catholyte compartment in step (B) is a borate, metaborate, tetraborate, perborate, or the hydrates or mixtures thereof.

45. The process of claim 40 wherein the quaternary ammonium boron oxide is prepared by reacting a quaternary ammonium salt with boric acid or boric acid anhydride.

46. The process of claim 40 wherein the cation exchange membrane comprises a perfluorosulfonic acid or a perfluorosulfonic acid/perfluorocarboxylic acid perfluorohydrocarbon polymer membrane.

47. The process of claim 40 wherein quaternary ammonium borohydride is recovered from the catholyte by crystallization, filtration or extraction.

48. The process of claim 40 wherein at least one hydrogenation catalyst is present in the catholyte compartment.

49. The process of claim 48 wherein the hydrogenation catalyst is nickel, cobalt, rhodium, copper, platinum, palladium or alloys, compounds or mixtures thereof.

50. The process of claim 40 wherein (E) the quaternary ammonium borohydride is recovered from the catholyte solution removed in step (D).

51. The process of claim 50 wherein the catholyte solution which remains after the quaternary ammonium borohydride is recovered in step (E) is charged to the anolyte compartment as anolyte.

52. The process of claim 40 wherein at least a portion of the anolyte is removed from the anolyte compartment after step (C); quaternary ammonium boron oxide is added to the removed anolyte solution, and the solution is charged to the catholyte compartment as catholyte.

* * * * *